US00PP36837P3

(12) United States Plant Patent
Olesen

(10) Patent No.: US PP36,837 P3
(45) Date of Patent: Jul. 22, 2025

(54) ROSE PLANT NAMED 'Poulpah126'

(50) Latin Name: *Rosa hybrida*
Varietal Denomination: Poulpah126

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/831,179

(22) Filed: Sep. 5, 2024

(65) Prior Publication Data

US 2025/0107470 P1 Mar. 27, 2025

(30) Foreign Application Priority Data

Sep. 22, 2023 (QZ) ..... PBR 20231978

(51) Int. Cl.
*A01H 5/02* (2018.01)
*A01H 6/74* (2018.01)

(52) U.S. Cl.
USPC ..... Plt./121
CPC ..... *A01H 6/749* (2018.05)

(58) Field of Classification Search
USPC ..... Plt./121
CPC ..... A01H 6/749; A01H 5/02
See application file for complete search history.

*Primary Examiner* — Keith O. Robinson

(57) ABSTRACT

A new garden rose plant of the Miniature class which has abundant, pink flowers and attractive foliage. This new and distinct variety has shown to be uniform and stable in the resulting generations from asexual propagation.

2 Drawing Sheets

Botanical designation: *Rosa hybrida.*

Variety denomination: 'Poulpah126'.

This application claims priority to Plant Breeder's Rights Application Number 2023/1978, which was filed at the Community Plant Variety Rights Office in the European Union on Sep. 22, 2023, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 1998 and the resulting seeds were planted in a controlled environment in Fredensborg, Denmark. The new variety, named 'Poulpah126', originated as a single seedling from the stated cross.

The new variety may be distinguished from its male pollen parent and female seed parent primarily by the following characteristics. The male pollen parent plant has light pink to near white flowers while the new variety has pink flowers. The female seed parent plant has red flowers while the new variety has pink flowers.

The objective of the hybridization of this rose variety was to create a new and distinct variety with unique qualities, such as:

1. Uniform and abundant pink flowers;
2. Vigorous, but compact growth when propagated on its own roots;
3. Exceptional disease resistance.

This combination of qualities is not present in previously available commercial cultivars of this type, known to the inventor, and distinguish 'Poulpah126' from all other varieties of which we are aware.

As part of the rose development program, Mogens N. Olesen germinated the seeds from the aforementioned hybridization during winter of 1998 and conducted evaluations on the resulting seedlings in a controlled environment in Fredensborg, Denmark. 'Poulpah126' was selected in the spring of 1999 by the inventor as a single plant from the progeny of the aforementioned hybridization.

Asexual reproduction of 'Poulpah126' by rooted cuttings was first done by Mogens N. Olesen in the nursery in Fredensborg, Denmark in July 1999. This initial and other subsequent asexual propagations conducted in controlled environments have demonstrated that the characteristics of 'Poulpah126' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah126'.

Specifically illustrated in FIG. 1 of the drawings are open flowers viewed from the side and above, petals detached revealing reproductive flower parts, a flower bud, and sepals detached.

Figure 1:
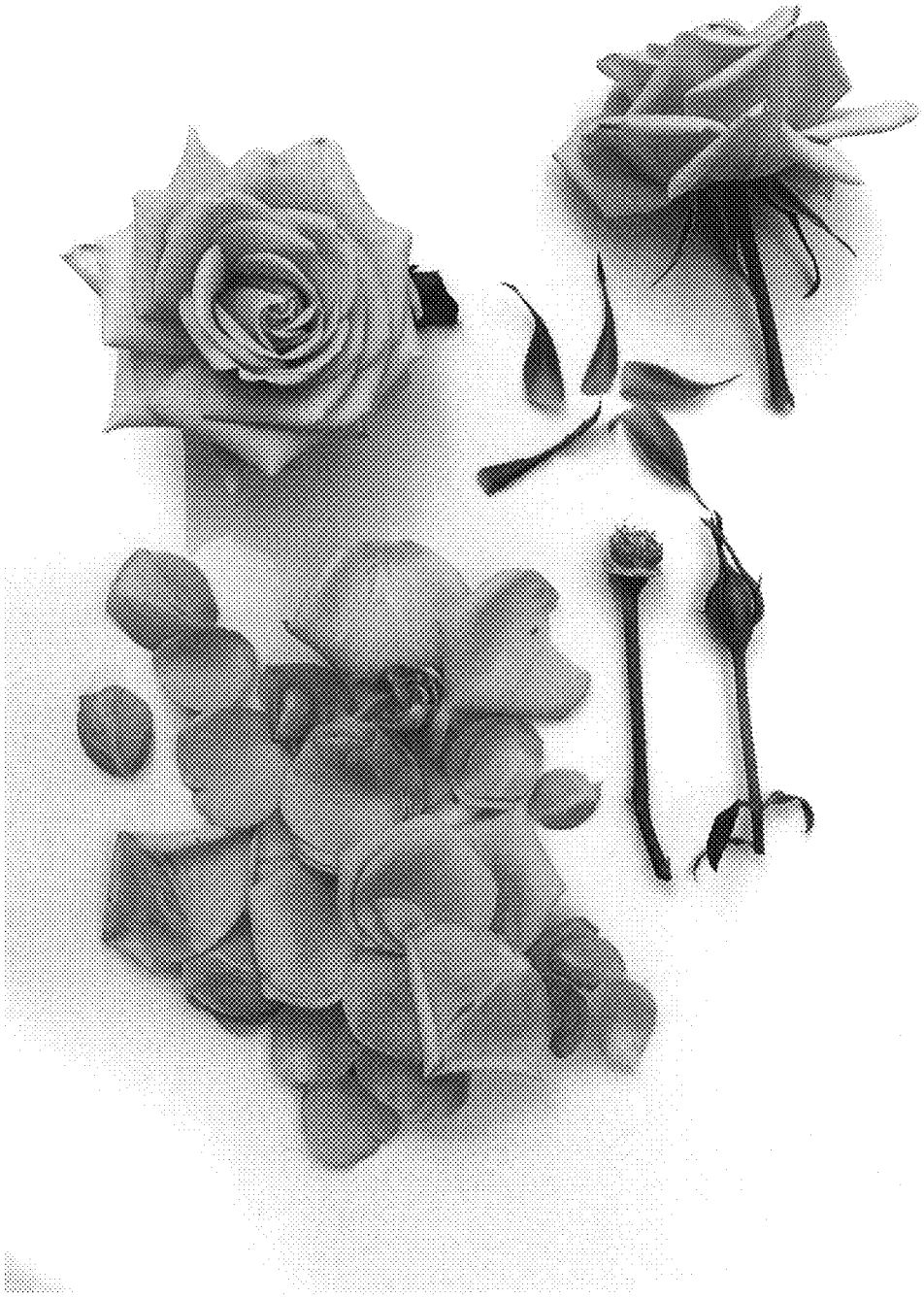
Figure 2:
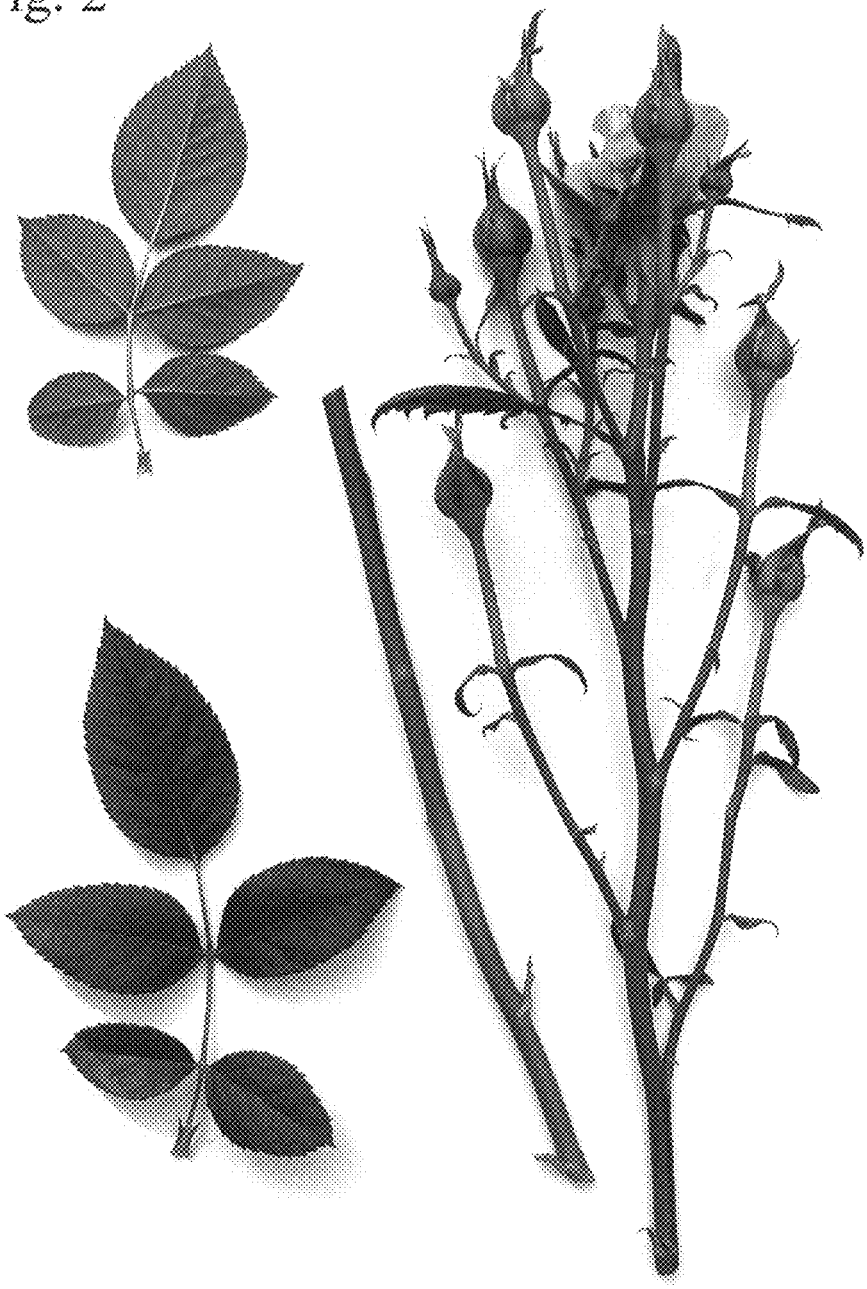

Specifically illustrated in FIG. 2 of the drawings are a cluster of flower buds on the branch, bare stem, and leaves. Plants shown are 6 months old.

DETAILED DESCRIPTION OF THE VARIETY

The following is a description of 'Poulpah126', as observed in its growth in a glasshouse in Odense Denmark.

Observed plants are 6 months of age, and were grown on their own roots in 23 cm pots. Color references are made using The Royal Horticultural Society (London, England) Colour Chart, 2001, except where common terms of color are used.

For a comparison, several physical characteristics of the rose variety 'Poulhi008', U.S. Pat. No. 15,722 are compared to the claimed plant. While 'Poulpah126' has 67 flower petals, 'Poulhi008' has 40 to 45 flower petals. Open flowers of 'Poulpah126' are generally Red-Purple Group 65B in color while 'Poulhi008' has a general tonality of Red Group 55B.

FLOWER AND FLOWER BUD

Blooming habit: Continuous.

Flower bud:

*Size*.—Upon opening, 30 mm in length from base of receptacle to end of bud. Bud diameter is 15 mm.

*Bud form*.—Ovoid.

*Bud color*.—As sepals divide petals are Red-Purple. Group 65A and Red-Purple Group 59C.

*Sepal inner surface*.—Color: Yellow-Green Group 146D. Surface: Lightly pubescent.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have no foliaceous appendages on three of the five sepals.

*Sepal size*.—About 30 mm long, 10 mm wide.

*Receptacle*.—Texture: Smooth. Size: 8 mm in height, 9 mm wide. Color: Yellow-Green Group 144A. Shape: Funnel.

*Pedicel*.—Surface: Rough with stipitate glands. Length: 40 mm average. Diameter: 3 mm on average. Color: Yellow-Green Group 144A. Strength: Strong.

*Peduncle*.—Length: 20 to 110 cm. Diameter: About 3 mm. Color: Yellow-Green Group 145A. Texture: Smooth.

Flower bud development: Flower buds are borne in clusters of 3 to 12 flower buds per stem.

Flower bloom:

*Fragrance*.—Slightly above moderate perfume.

*Duration*.—The blooms have a duration on the plant of approximately 21 days. Petals fall cleanly away from plant after flowers have fully matured.

*Size*.—Flower diameter is about 80 mm when open. Flower depth is 40 mm.

*Flower shape*.—High centered, very double, with a high pointed center which is tightly closed.

*Shape of flower, side view*.—The upper portion is concave. The lower portion is flat convex.

Petalage: Under normal conditions, flowers have about 67 petals.

General tonality of flower: Open flowers are Red-Purple Group 65B.

Petal color:

*Upon opening, outer petals*.—Upper surface: Red-Purple Group 65B with light streaks of Red-Purple Group 64C. Lower surface: Red-Purple Group 65A and B with streaks of Red-Purple Group 64C.

*Upon opening, inner petals*.—Upper surface: Red Group 48C. Lower surface: Red Group 51A with other intonations Red Group 38B.

*Basal petal spots, upon opening*.—Upper surface: Yellow Group 8C. Lower surface: Yellow Group 4D to 8D.

*After opening, outer petals*.—Upper surface: Marginal Red-Purple Group 69B with shades of Red-Purple Group 62A. Lower surface: Red-Purple Group 65B with streaks of Red-Purple Group 64D.

*After opening, inner petals*.—Upper surface: Red Group 49B with streaks of Red-Purple Group 62A. Lower surface: Red Group 38B with streaks of Red Group 54A and Yellow Group 10C.

*Basal petal spots, after opening*.—Upper surface: Yellow Group 8C. Lower surface: Yellow Group 8D.

Petals:

*Petal reflex*.—Strong bilateral.

*Margin*.—Entire and uniform. Moderate undulations.

*Shape*.—Broad and elliptic. Apex shape: Round. Base shape: Round.

*Size*.—About 42 mm (l)×55 mm (w).

*Texture*.—Smooth.

*Thickness*.—Average.

Petaloids:

*Size*.—About 16 mm (l) by 10 mm (w).

*Quantity*.—18 average.

*Shape*.—Elliptical and irregular generally with an acute base and rounded apices. Undulations in the margins.

*Color*.—Lower surface is Red Group 37B with streaks of Red Group 53D. The upper surface is Red Group 39B with streaks of Red Group 53D and Yellow Group 8C. Basal petal spots are Yellow Group 8A on both sides.

Reproductive flower parts:

*Pollen*.—None observed.

*Anthers*.—Size: 2 mm in length. Color: Yellow-Orange Group 18B. Quantity: 58 on average.

*Filaments*.—Color: Yellow Group 13B and Orange Red Group 34C. Length: 5 mm.

*Pistils*.—Length: 9 mm. Quantity: 36 on average.

*Stigmas*.—Color: Yellow-Green Group 145D.

*Styles*.—Color: Yellow-Green Group 145D with intonations of Red-Purple Group 58A.

*Location of stigmas*.—Inferior in location relative to the length of the filaments and the height of the anthers.

*Hips*.—None Observed.

PLANT

Plant growth: Upright, bushy. Plants are 55 cm in height, and 50 cm wide.

Stems:

*Color of juvenile growth*.—Yellow-Green Group 144B.

*Color of mature growth*.—Yellow-Green Group 144A.

*Length*.—Canes are about 40 cm from the base of the plant to the flowering portion.

*Diameter*.—About 6 mm.

*Internodes*.—On mature canes about 54 mm between nodes.

*Surface texture*.—Young wood: Smooth. Older wood: Smooth.

Long prickles:

*Incidence*.—None.

Plant foliage:

*Compound leaf.*—146 mm (l)×111 (w).

*Quantity.*—2 or 3 leaves per 10 cm of stem on average.

*Leaf bearing angle to the stem.*—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 10 mm long, 4 mm wide. Quantity: 2 per compound leaf. Shape: Linear, slightly broad based with outward extending apices. Margins: Finely serrated. Color: Yellow-Green Group 144A.

*Petiole*.—Length: 25 mm. Diameter: 1.5 mm. Upper surface color: Yellow-Green Group 144A. Lower surface color: Yellow-Green Group 144A.

*Rachis*.—Length: About 53 mm. Upper surface color: Yellow-Green Group 144A. Lower surface color: Yellow-Green Group 145B.

*Leaflet*.—Quantity: Normally 5 leaflets. Margins: Serrated. Size: Terminal leaflets are about 72 mm long, 36 mm wide. Shape: Generally elliptical. Base: Rounded. Apex: Aristate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpah126' substantially as described and illustrated herein.

* * * * *